(12) United States Patent
Kehdy et al.

(10) Patent No.: US 8,894,667 B2
(45) Date of Patent: Nov. 25, 2014

(54) ENDOSCOPIC CLOSURE DEVICE

(75) Inventors: Farid Kehdy, Prospect, KY (US);
Guruprasad A. Giridharan, Louisville, KY (US); Erica J. Wells, Jeffersonville, IN (US); Kenny J. King, Barlow, KY (US); Lindsay N. Strotman, Louisville, KY (US); William R. Ross, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 280 days.

(21) Appl. No.: 13/044,334

(22) Filed: Mar. 9, 2011

(65) Prior Publication Data

US 2012/0059395 A1   Mar. 8, 2012

Related U.S. Application Data

(60) Provisional application No. 61/312,070, filed on Mar. 9, 2010.

(51) Int. Cl.
*A61B 17/04* (2006.01)
*A61B 17/00* (2006.01)
*A61B 17/06* (2006.01)

(52) U.S. Cl.
CPC ......... *A61B 17/0057* (2013.01); *A61B 17/0401* (2013.01); *A61B 2017/00398* (2013.01); *A61B 2017/00663* (2013.01); *A61B 2017/0417* (2013.01); *A61B 2017/047* (2013.01); *A61B 2017/0472* (2013.01); *A61B 2017/0498* (2013.01); *A61B 2017/06052* (2013.01); *A61B 2017/06076* (2013.01)
USPC ....................................................... 606/144

(58) Field of Classification Search
CPC ................. A61B 17/0057; A61B 2017/00637; A61B 2017/047; A61B 2017/0472; A61B 2017/0498; A61B 2017/06076
USPC ........................................... 606/139, 144–145
See application file for complete search history.

(56) References Cited

U.S. PATENT DOCUMENTS

| | | |
|---|---|---|
| 5,330,503 A | 7/1994 | Yoon |
| 5,356,424 A | 10/1994 | Buzerak et al. |
| 5,509,923 A | 4/1996 | Middleman et al. |
| 5,653,716 A | 8/1997 | Malo et al. |
| 5,669,490 A | 9/1997 | Colligan et al. |
| 5,935,138 A | 8/1999 | McJames, II et al. |

(Continued)

OTHER PUBLICATIONS

ISA/US, International Search Report for corresponding International Application No. PCT/US2011/027757, mailed May 13, 2011.

*Primary Examiner* — Julian W Woo
*Assistant Examiner* — Shaun L David
(74) *Attorney, Agent, or Firm* — Stites & Harbison, PLLC; David W. Nagle, Jr.

(57) ABSTRACT

An endoscopic closure device comprises: a coupling member; a helical needle mounted to the coupling member and carrying a suture; and a plurality of grasping needles, each of said plurality of grasping needles moveable between a storage position and a deployed position. The plurality of grasping needles is configured to be (a) advanced in the storage position into a luminal defect, (b) moved into the deployed position, and (c) then refracted from the luminal defect, thus pulling and drawing tissue surrounding the luminal defect together. Then, upon rotation of the coupling member and the helical needle, the helical needle is driven into and pierces the tissue, carrying the suture through the tissue.

5 Claims, 20 Drawing Sheets

(56) References Cited

U.S. PATENT DOCUMENTS

| | | |
|---|---|---|
| 6,113,610 A * | 9/2000 | Poncet .................. 606/139 |
| 6,554,845 B1 | 4/2003 | Fleenor et al. |
| 6,626,917 B1 | 9/2003 | Craig |
| 7,144,401 B2 | 12/2006 | Yamamoto et al. |
| 7,637,918 B2 | 12/2009 | Dant |
| 2001/0023352 A1 | 9/2001 | Gordon et al. |
| 2004/0002699 A1 | 1/2004 | Ryan et al. |
| 2006/0173491 A1 | 8/2006 | Meade et al. |
| 2006/0212048 A1 | 9/2006 | Crainich |
| 2006/0253127 A1 | 11/2006 | Bjerken |
| 2008/0249566 A1 * | 10/2008 | Harris et al. ............. 606/220 |
| 2009/0275960 A1 | 11/2009 | Provenza et al. |
| 2010/0036395 A1 | 2/2010 | Miller |
| 2010/0121140 A1 | 5/2010 | Hashiba et al. |

* cited by examiner

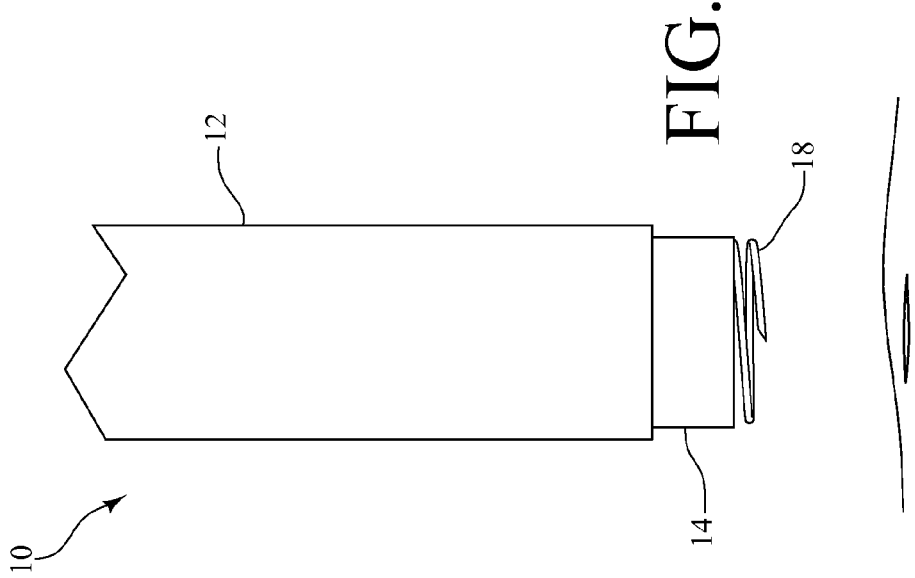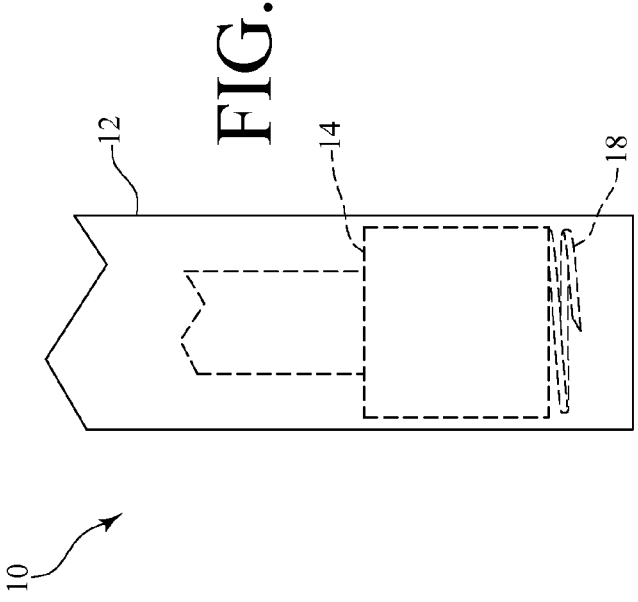

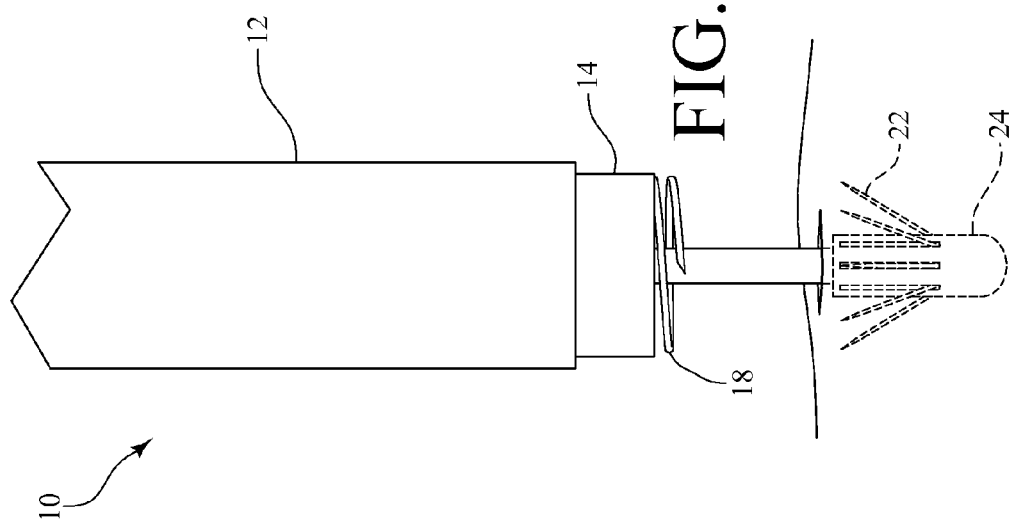
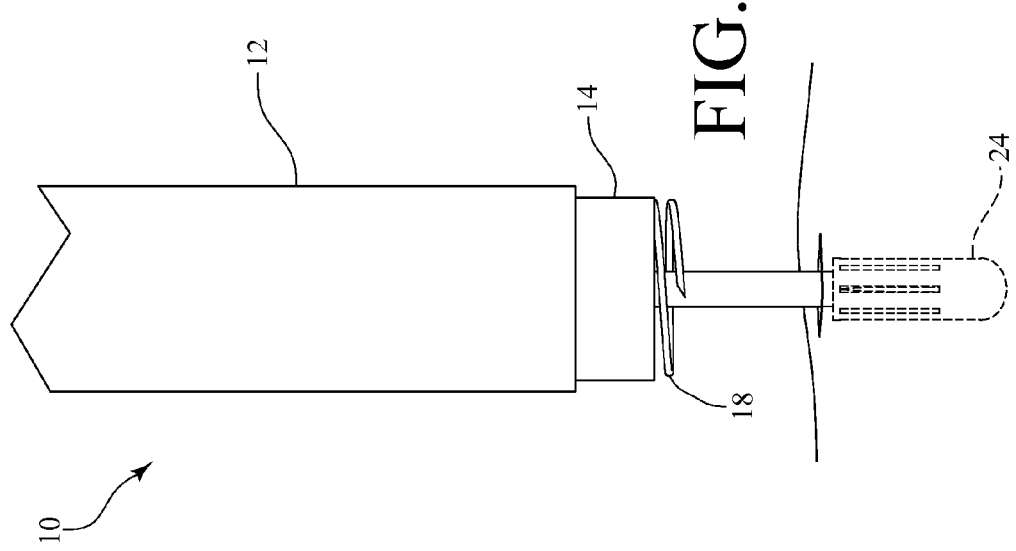

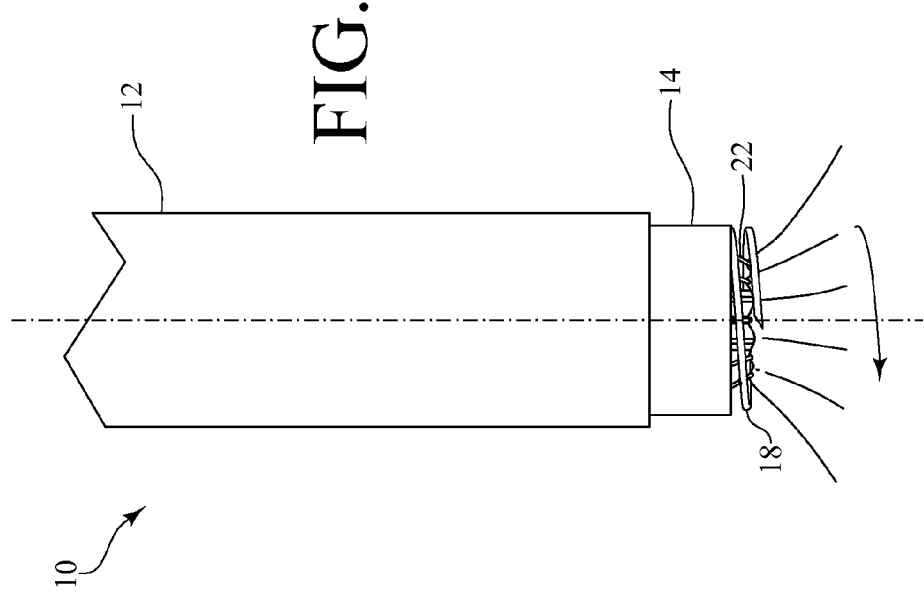
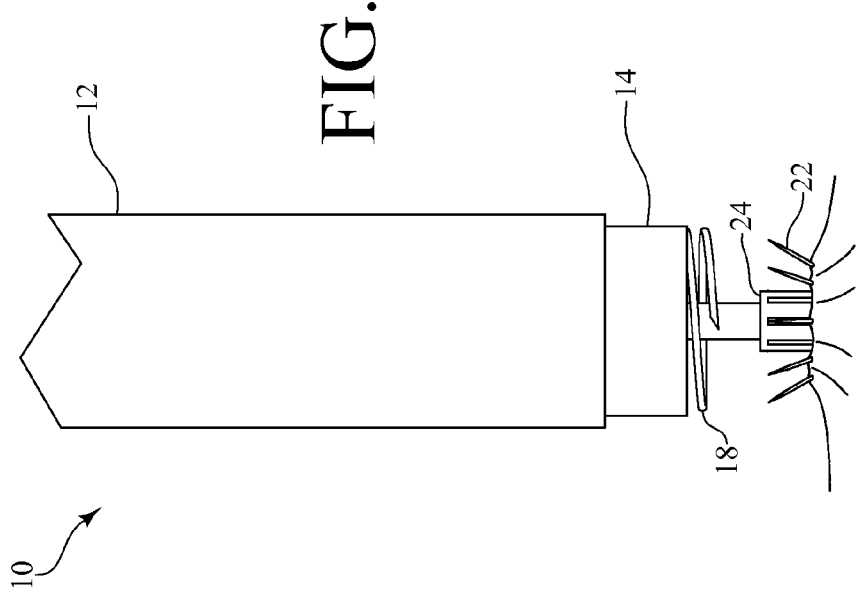

ENDOSCOPIC CLOSURE DEVICE

CROSS-REFERENCE TO RELATED APPLICATIONS

The present application claims priority to U.S. Provisional Patent Application Ser. No. 61/312,070 filed on Mar. 9, 2010, the entire disclosure of which is incorporated herein by reference.

BACKGROUND OF THE INVENTION

Natural Orifice Transluminal Endoscopic Surgery (NOTES) is an emerging technology that allows a surgeon to insert surgical instruments through a natural orifice (such as the mouth, anus, or vagina) and then access the abdominal cavity through a defect created in the stomach, colon, bladder or vagina, thus avoiding any external incisions or scars. NOTES has been performed on experimental pig models using various surgical procedures and flexible endoscopy instruments. A major hurdle to transform this technology to the human patient is the closure of the luminal defect created to access the abdominal cavity. Suture closure is still the preferred means of closing such a luminal defect, but is technically challenging because of space constraints in the endoscope. Furthermore, when creating an incision through the gastrointestinal tract, whether it is the stomach or the colon, a subsequent leak could lead to catastrophic problems, and thus, reliability of the closure is of utmost concern.

SUMMARY OF THE INVENTION

The present invention is an endoscopic closure device that can be used for closing a luminal defect, including, but not limited to, a gastric perforation or other luminal defect created to access the abdominal cavity for a NOTES procedure.

In one embodiment, an endoscopic closure device made in accordance with the present invention includes an outer sheath (or overtube) that encloses a coupling member, which is adapted for movement within and relative to the outer sheath along the longitudinal axis of the endoscopic closure device. A helical needle is then mounted to the distal end of the coupling member. A plunger assembly is housed within the coupling member, with the plunger assembly being adapted for movement within and relative to the coupling member along the longitudinal axis of the endoscopic closure device.

The plunger assembly includes a plurality of grasping needles positioned within a needle housing. The plunger assembly further includes a plunger that is adapted for movement along the longitudinal axis of the plunger assembly by a rod connected to the plunger. By moving the plunger downward, it engages and moves the grasping needles from a storage position within the needle housing to a deployed position in which they extend through the walls of the needle housing.

In practice, the endoscopic closure device is first placed in proximity to the luminal defect. The coupling member and helical needle are then pushed out of the outer sheath and advanced toward the luminal defect. The plunger assembly is then advanced toward the luminal defect, extending beyond the helical needle and into the luminal defect. The plunger is then moved downward, preferably by advancing the rod that is connected to the plunger, which causes the plunger to engage and move the grasping needles to the deployed position in which they extend through the walls of the needle housing. The plunger assembly is then retracted and pulled back toward the helical needle, pulling and drawing the tissue surrounding the luminal defect together within the cylindrical cavity bounded by the helical needle. The coupling member and the helical needle are then rotated, so that the helical needle is driven into and pierces the tissue, carrying a suture through the tissue.

With respect to the rotation of the helical needle, such rotation can be achieved in a variety of different manners, including manually, with a user grasping and rotating the coupling member, or by using a motor and gearing arrangement.

It is also contemplated that various means of deploying the grasping needles could be incorporated into the endoscopic closure device. For example, in another embodiment, a pulling action deploys the grasping needles. Specifically, pulling on a rod connected to the plunger causes the plunger to move upward, engage, and press against the base of each grasping needle. This causes each base to pivot such that the grasping needles are moved from the storage position within the needle housing to the deployed position in which they extend through the walls of the needle housing.

In another embodiment, an endoscopic closure device made in accordance with the present invention includes a handle portion. The handle portion defines a central channel along its length. At a first end of the central channel, the handle portion defines a cavity for receiving a first (or rear) adjustment knob. At the opposite end of the central channel, the handle portion defines a cavity for receiving a second (or front) adjustment knob.

The second adjustment knob is mounted for linear and rotational movement within the cavity relative to the handle portion. Furthermore, the second adjustment knob is connected to a first (or external) hollow shaft that extends away from the handle portion of the endoscopic closure device, such that the second adjustment knob and the first hollow shaft rotate together. A coupling member is connected to the distal end of this first hollow shaft, and thus also moves and/or rotates with the second adjustment knob and the first hollow shaft. Finally, a helical needle is mounted to the coupling member.

The endoscopic closure device also includes a second (or internal) hollow shaft that is fixed to the handle portion and then extends through the second adjustment knob and through the first hollow shaft. A needle housing is connected to the distal end of the second hollow shaft.

The first adjustment knob is connected to a rod that extends through the central channel of handle portion, through the second hollow shaft, and into the needle housing, where it is connected to a plunger. A plurality of grasping needles is positioned within the needle housing in a storage position. Furthermore, one or more elastomeric rings is positioned around the plurality of grasping needles to bias them into the storage position.

The plunger is adapted for movement within and along the longitudinal axis of the needle housing. By moving the plunger downward, it engages and moves the grasping needles from the storage position within the needle housing to the deployed position in which they extend through the walls of the needle housing.

With respect to the movement of the plunger, such movement is controlled by the first adjustment knob. By advancing the first adjustment knob into the cavity relative to the handle portion, the plunger is moved downward to engage and move the grasping needles. Alternatively, the first adjustment knob may be provided with threads that mate with corresponding threads defined by the handle portion. Thus, by turning the first adjustment knob in one direction (e.g., clockwise), the first adjustment knob advances into the handle portion and moves the plunger downward to engage and move the grasping needles. By turning the first adjustment knob in the opposite direction (e.g., counterclockwise), the plunger is moved upward and away from the grasping needles, and the grasping needles return to the storage position.

Again, the endoscopic closure device is placed in proximity to the luminal defect, preferably over a guide wire. As the endoscopic closure device is advanced into position, the needle housing is extended into the luminal defect, with a user grasping and manipulating the handle portion of the endoscopic closure device to position it in the luminal defect, with the needle housing below the surface of the surrounding tissue. The plunger is then moved downward by advancing (or turning) the first adjustment knob. The plunger thus engages and moves the grasping needles to the deployed position in which the grasping needles extend through the walls of the needle housing. The user can then pull up on the handle portion of the endoscopic closure device to pull and draw the tissue surrounding the luminal defect together with the grasping needles.

Next, the user can manipulate the second adjustment knob, moving it downward and away from the handle portion of the endoscopic closure device. Since the second adjustment knob is connected to the first hollow shaft, which, in turn, is connected to the coupling member, the helical needle is thus advanced toward the grasping needles. As a result, the surrounding tissue is now within a cylindrical cavity bounded by the helical needle. Then, by rotating the second adjustment knob relative to the handle portion, the first hollow shaft and the coupling member are also rotated, so that the helical needle is driven into and pierces the tissue, carrying a suture through the tissue.

DESCRIPTION OF THE DRAWINGS

FIGS. 5A-5G are side views of the exemplary endoscopic closure device of FIG. 1, illustrating the use of the exemplary endoscopic closure device;

DETAILED DESCRIPTION OF THE INVENTION

The present invention is an endoscopic closure device that can be used for closing a luminal defect, including, but not limited to, a gastric perforation or other luminal defect created to access the abdominal cavity for a NOTES procedure.

Figure 1:
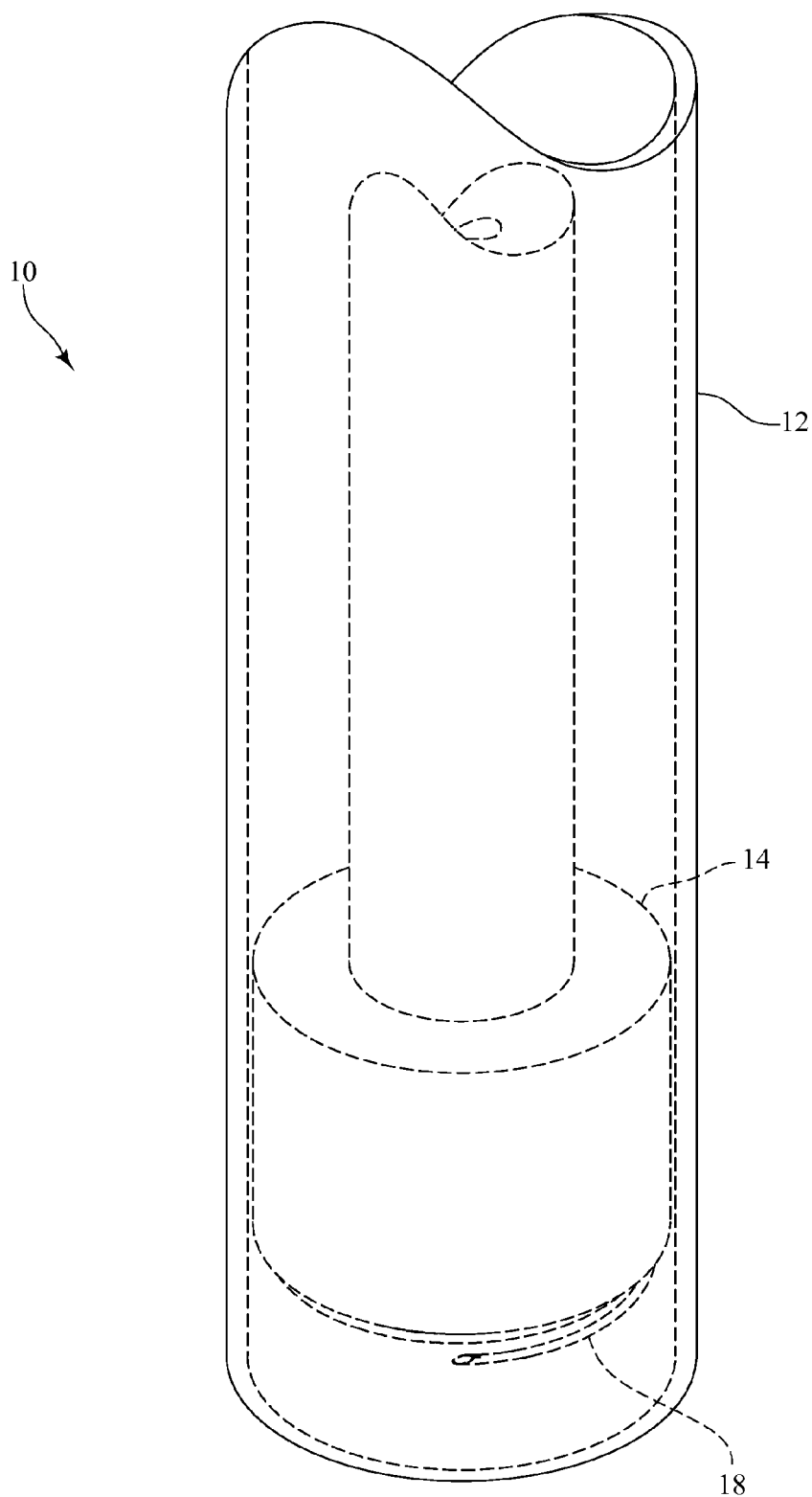
FIG. 1 is a perspective view of an exemplary endoscopic closure device made in accordance with the present invention.

FIG. 1 is a perspective view of an exemplary endoscopic closure device 10 made in accordance with the present invention. As illustrated in FIG. 1, the endoscopic closure device 10 includes an outer sheath 12 (or overtube) that encloses a coupling member 14, which is adapted for movement within and relative to the outer sheath 12 along the longitudinal axis of the endoscopic closure device 10. A helical needle 18 is then mounted to the distal end of the coupling member 14, the function of which will be described below.

Figure 2:
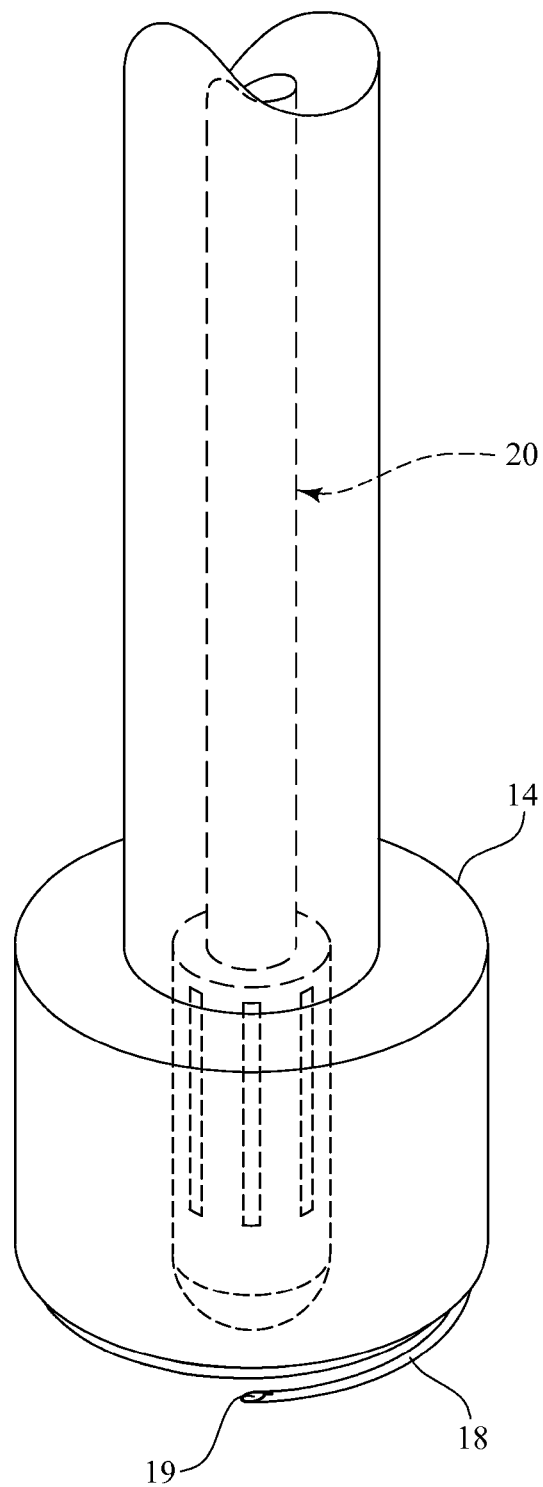
FIG. 2 is another perspective view of the exemplary endoscopic closure device of FIG. 1, but without the outer sheath, and further illustrating a plunger assembly housed within the coupling member.

FIG. 2 is another perspective view of the exemplary endoscopic closure device 10 without the outer sheath 12, and further illustrating a plunger assembly 20 housed within the coupling member 14, with the plunger assembly 20 being adapted for movement within and relative to the coupling member 14 along the longitudinal axis of the endoscopic closure device 10.

Figure 3:
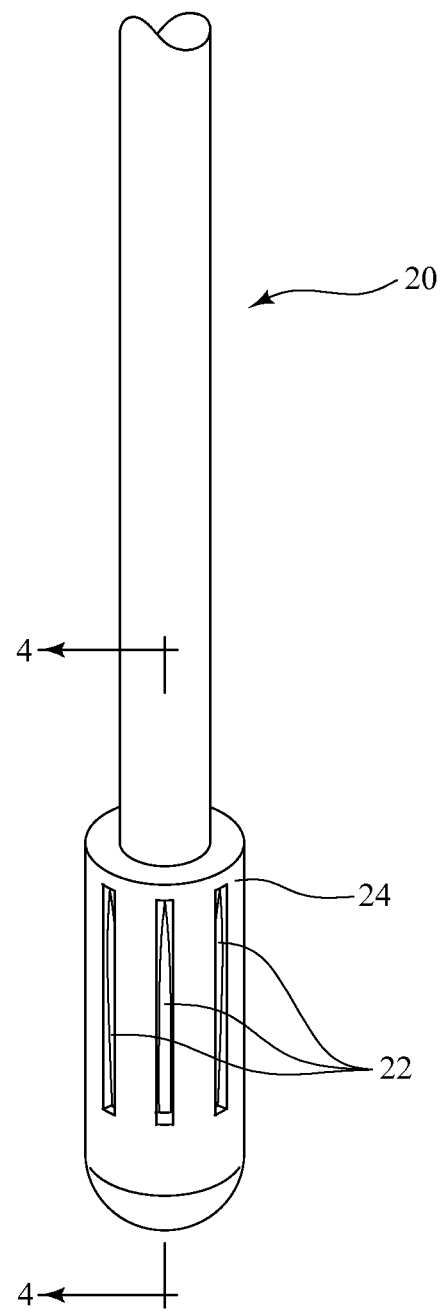
FIG. 3 is a perspective view of the plunger assembly of the exemplary endoscopic closure device of FIG. 1.

FIG. 3 is a perspective view of the plunger assembly 20 of the exemplary endoscopic closure device 10, which includes a plurality of grasping needles 22, the function of which will be described below.

Figure 4A:
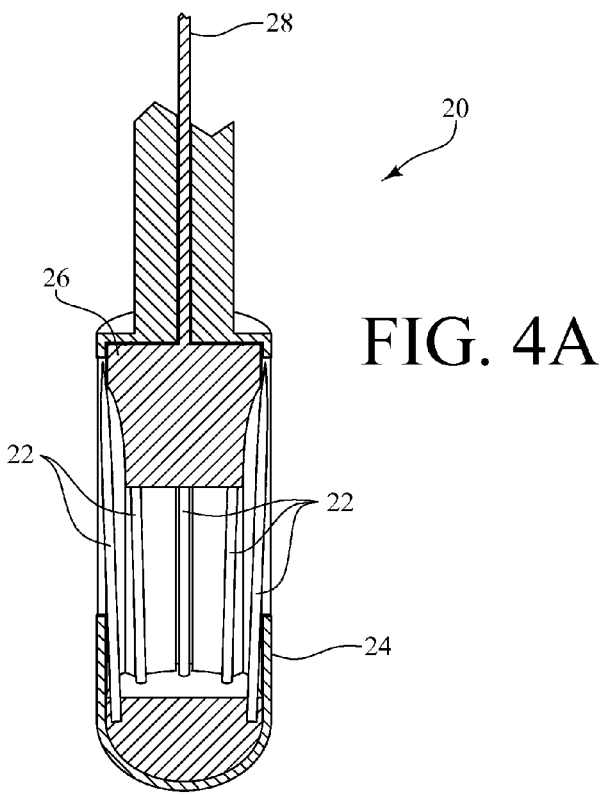
FIG. 4A is a sectional view of the plunger assembly of FIG. 3 taken along line 4-4 of FIG. 3, with the grasping needles positioned within a needle housing in a storage position.
Figure 4B:
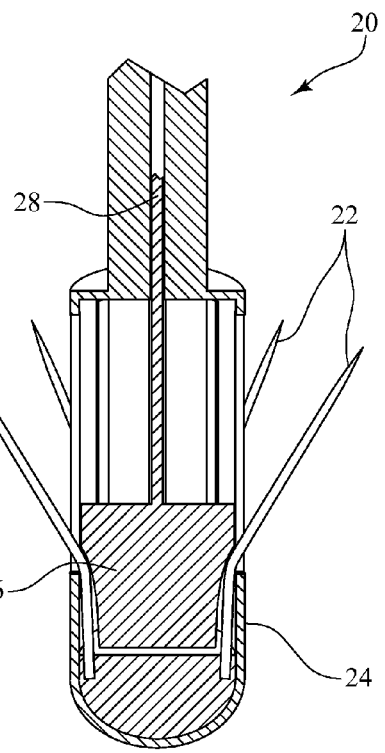
FIG. 4B is a sectional view of the plunger assembly similar to FIG. 4A, but with the grasping needles in a deployed position.

FIG. 4A is a sectional view of the plunger assembly 20 taken along line 4-4 of FIG. 3, with the grasping needles 22 positioned within a needle housing 24 in a storage position. FIG. 4B is a sectional view of the plunger assembly 20 similar to FIG. 4A, but with the grasping needles 22 in a deployed position. As illustrated in FIGS. 4A and 4B, there is a plunger 26 that is adapted for movement along the longitudinal axis of the plunger assembly 20 by a rod 28 connected to the plunger 26. By moving the plunger 26 downward, it engages and moves the grasping needles 22, which are preferably constructed of a substantially flexible metal (such as nitinol, an alloy of nickel and titanium) from the storage position within the needle housing 24 (FIG. 4A) to the deployed position in which they extend through the walls of the needle housing 24 (FIG. 4B).

Figure 5G:
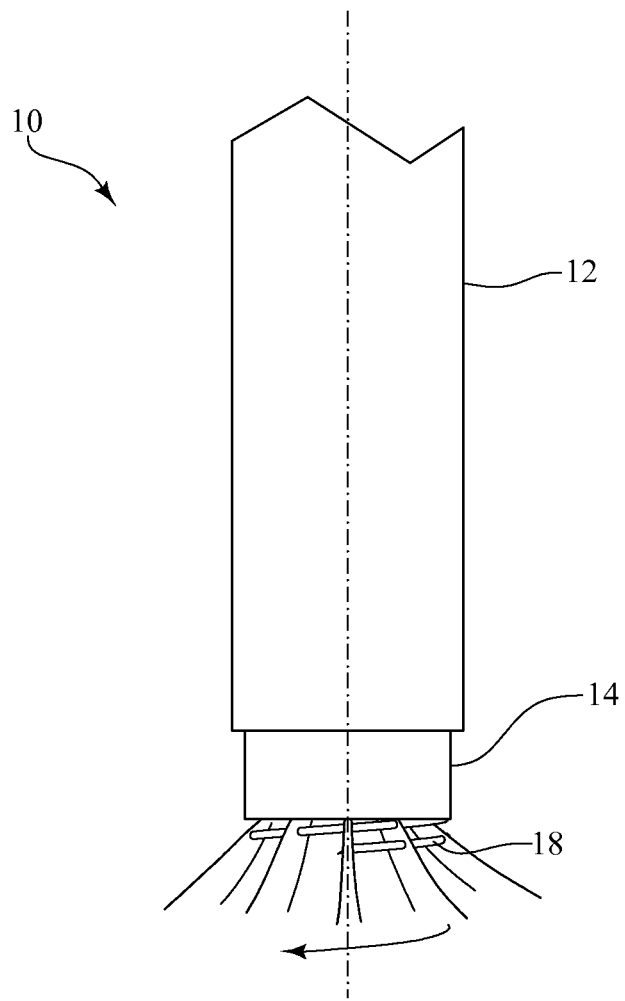

FIGS. 5A-5G illustrate the use of the exemplary endoscopic closure device 10. The endoscopic closure device 10 is first placed in proximity to the luminal defect. The coupling member 14 and helical needle 18 are pushed out of the outer sheath 12 and advanced toward the luminal defect, as illustrated in FIG. 5B. The plunger assembly 20 is then advanced toward the luminal defect, extending beyond the helical needle 18 and into the luminal defect, as illustrated in FIG. 5C. The plunger 26 (illustrated in FIGS. 4A and 4B) is then moved downward, preferably by advancing the rod 28 that is connected to the plunger 26, which causes the plunger 26 to engage and move the grasping needles 22 to the deployed position in which they extend through the walls of the needle housing 24, as illustrated in FIG. 5D. The plunger assembly 20 is then refracted and pulled back toward the helical needle 18, as illustrated in FIG. 5E, pulling and drawing the tissue surrounding the luminal defect together within the cylindrical cavity bounded by the helical needle 18, as illustrated in FIG. 5F. The coupling member 14 and the helical needle 18 are then rotated, so that the helical needle 18 is driven into and pierces the tissue, carrying a suture through the tissue, as illustrated in FIG. 5G. In this regard, the helical needle 18 passes through the tissue multiple times, thus creating a "purse string" suture.

With respect to the rotation of the helical needle 18, such rotation can be achieved in a variety of different manners without departing from the spirit and scope of the present invention. In the exemplary embodiment described above with reference to FIGS. 1-3, 4A-4B, and 5A-5G, the helical needle 18 rotates with the coupling member 14, and it is contemplated that such rotation could be achieved manually, with a user grasping and rotating the coupling member 14 (or some form of extension of the coupling member 14) relative to the outer sheath 12.

Figure 6:
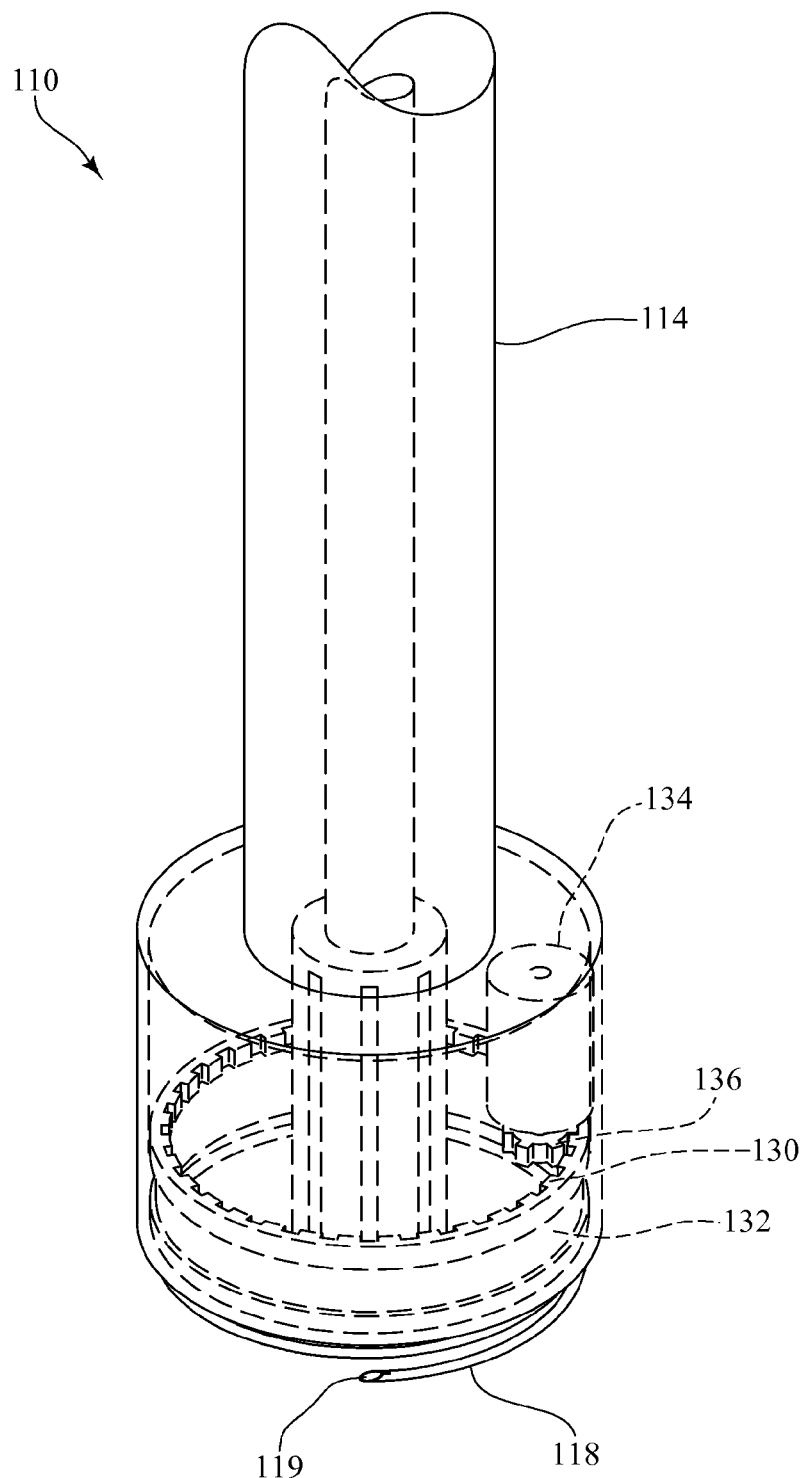
FIG. 6 is a perspective view of another exemplary endoscopic closure device made in accordance with the present invention.
Figure 7:
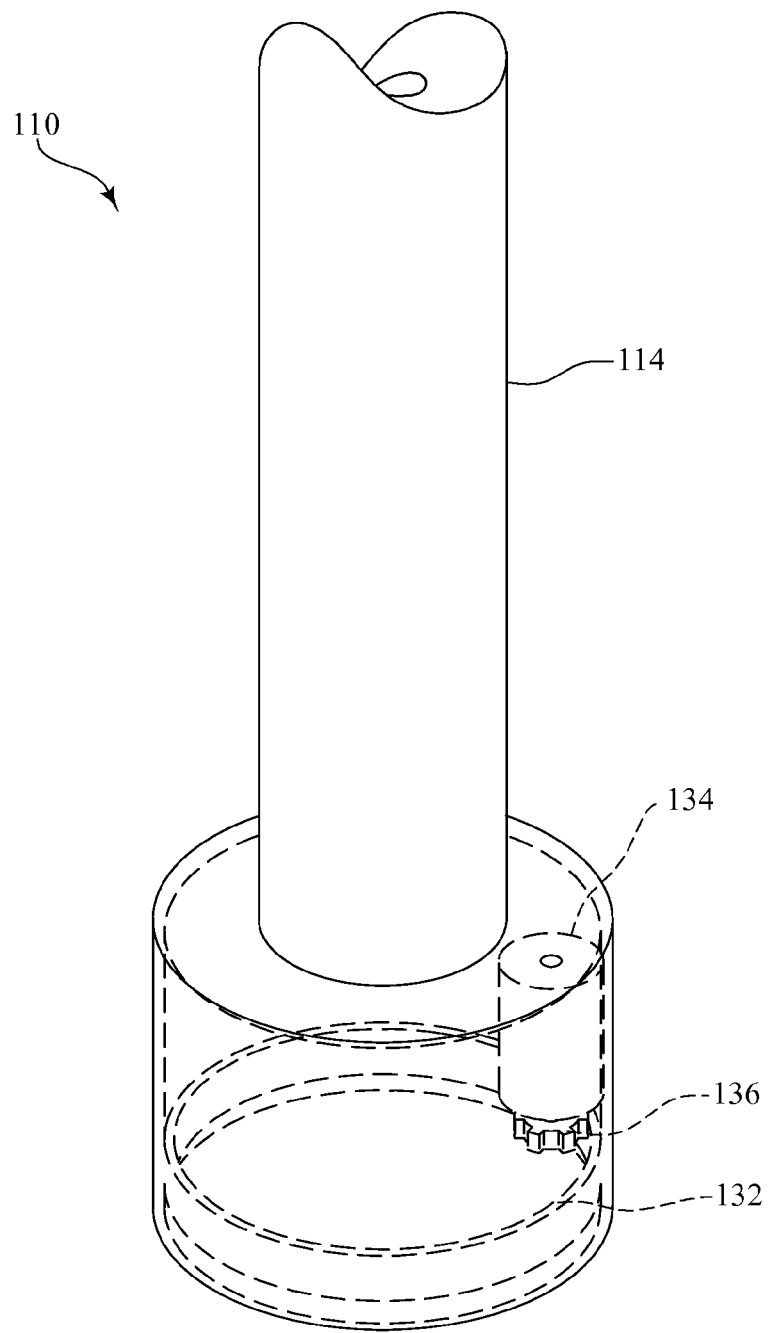
FIG. 7 is another perspective view of the other exemplary endoscopic closure device of FIG. 6, with certain components removed for clarity.
Figure 8:
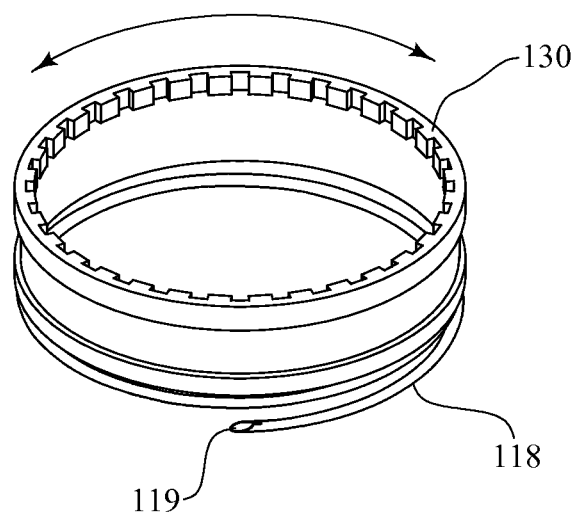
FIG. 8 is a perspective view of the helical needle and the ring gear of the other exemplary endoscopic closure device of FIG. 6.

FIGS. 6-8 illustrate another exemplary endoscopic closure device 110 (with the outer sheath removed for clarity) in which the helical needle 118 rotates relative to the coupling member 114. Specifically, in this embodiment, the helical needle 118 is secured to a ring gear 130. The ring gear 130 is received in and adapted for rotation with respect to a retaining ring 132, with the retaining ring 132 being secured to the inner, circumferential wall of the coupling member 114. A motor 134 is also secured to the inner, circumferential wall of the coupling member 114 and drives a gear 136 that engages the ring gear 130. Thus, activation of the motor 134 causes rotation of the gear 136, which, in turn, then causes rotation of the ring gear 130 and the helical needle 118.

Irrespective of the particular manner in which rotation of the helical needle 18, 118 is achieved, once the helical needle 18, 118 has been rotated to create the "purse string" suture around the luminal defect, the suture must be disengaged from the helical needle 18, 118. In the exemplary embodiments described above, the helical needle 18, 118 is hollow with an opening 19, 119 at its distal end. For example, the helical needle 18, 118 may be made of surgical stainless steel, with an overall outer diameter of 2-5 cm.

Figure 9:
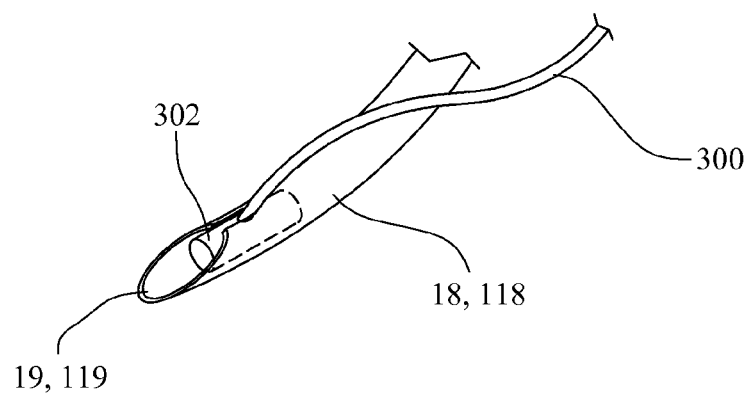
FIG. 9 is an enlarged perspective view of the end of the helical needle of the exemplary endoscopic closure devices of FIG. 1 or 6, along with a T-tag.
Figure 10:
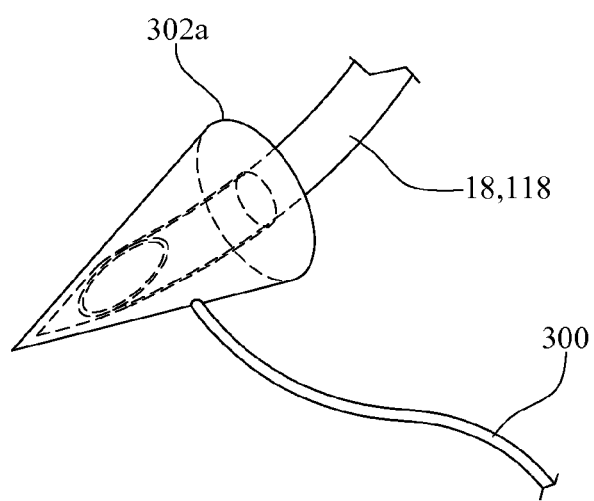
FIG. 10 is an enlarged perspective view of the end of the helical needle of the exemplary endoscopic closure devices of FIG. 1 or 6, along with a T-tag in the form of a cone.
Figure 11:
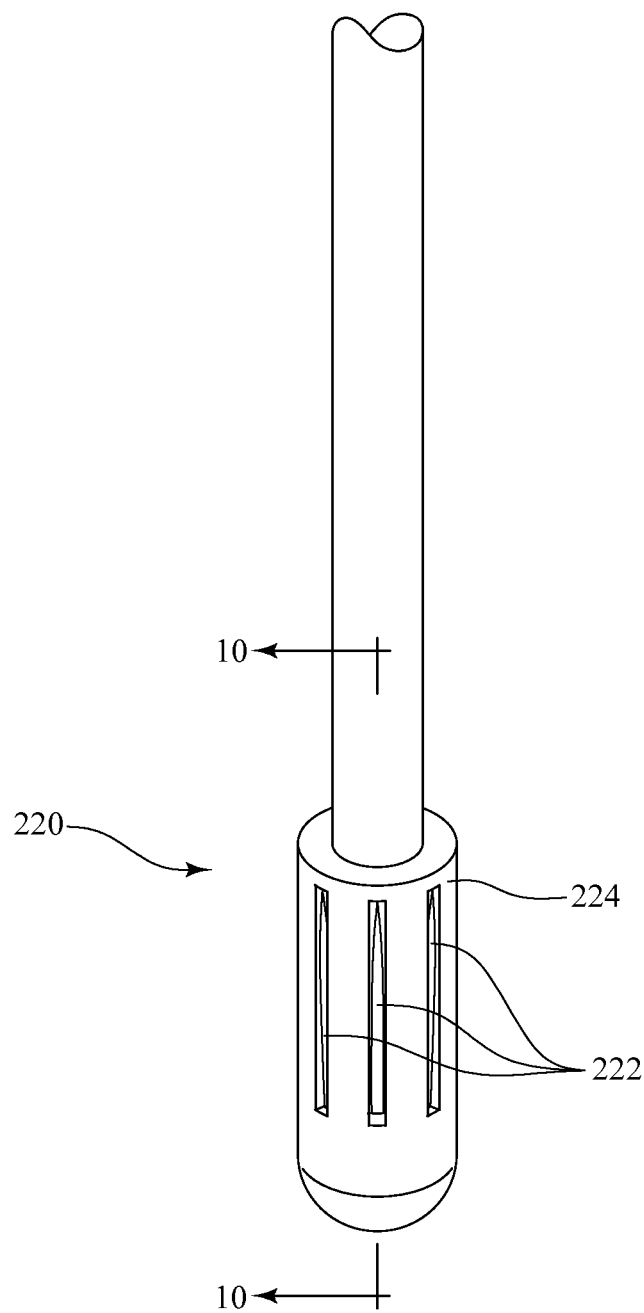
FIG. 11 is a perspective view of an alternate plunger assembly and needle housing.

Referring now to the enlarged perspective view of the helical needle 18, 118 in FIG. 9, a suture 300 with a T-tag 302 at its distal end can be loaded into the helical needle 18, 118. Thus, as the helical needle 18, 118 is rotated, the suture 300 is carried through the tissue, with the T-tag 302 serving as an anchor. Then, once the "purse string" suture has been created, the T-tag 302 is dislodged from the helical needle 18, 118. For example, this can be achieved by pushing the T-tag 302 out of the helical needle 18, 118 using a wire or similar implement advanced through the hollow helical needle 18, 118. Alternatively, and referring now to FIG. 10, the T-tag 302a may be in the form of a cone that is positioned on the end of the helical needle 18, 118. This T-tag 302a would remain at the end of the helical needle 18, 118 as the helical needle 18, 118 is rotated and driven through the tissue. However, once the suture 300 has been completed, the helical needle 18, 118 would then be rotated in the opposite direction to withdraw the helical needle 18, 118 from the tissue. The conical shape of the T-tag 302a would cause it to engage and remain in the tissue, slipping off of the end of the helical needle 18, 118 as the helical needle 18, 118 is withdrawn from the tissue It is also contemplated that various means of deploying the grasping needles could be incorporated into the endoscopic closure device without departing from the spirit and scope of the present invention. For example, in the exemplary embodiment described above with reference to FIGS. 1-3, 4A-4B, and 5A-5G, a plunger 26 is used to move the grasping needles 22 from the storage position to the deployed position. Alternatively, FIGS. 11-15 illustrate an alternate plunger assembly 220, in which the grasping needles 222 are again positioned within a needle housing 224 in a storage position. As best illustrated in the sectional views of FIGS. 12A and 12B, in this embodiment, there is a plunger 226 that is adapted for movement along the longitudinal axis of the plunger assembly 220 by a rod 228 connected to the plunger 226. However, in this embodiment, a pulling action deploys the grasping needles 222. Specifically, pulling on the rod 228 causes the plunger 226 to move upward, engage, and press against the base 223 of each grasping needle 222. This causes each base 223 to pivot such that the grasping needles 222 are moved from the storage position within the needle housing 224 (FIG. 12A) to the deployed position in which they extend through the walls of the needle housing 224 (FIG. 12B).

Figure 13:
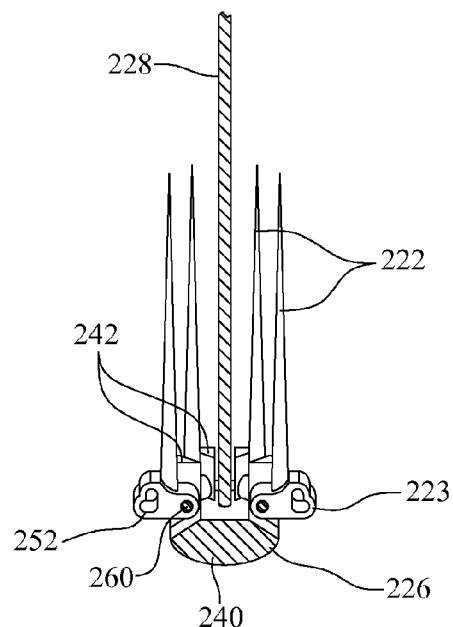
FIG. 13 is a sectional view of the alternate plunger assembly of FIG. 11.
Figure 14:
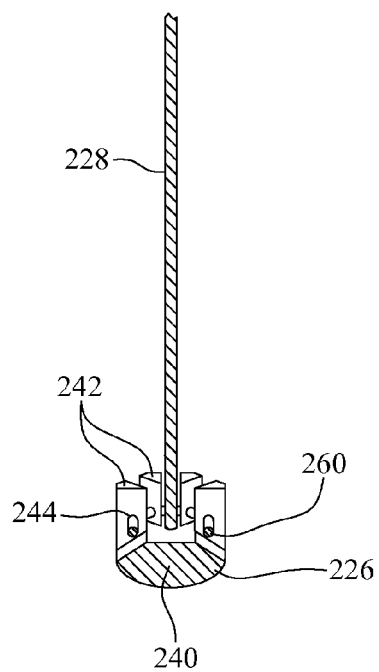
FIG. 14 is a sectional view of the plunger and rod of the alternate plunger assembly of FIG. 11.
Figure 15:
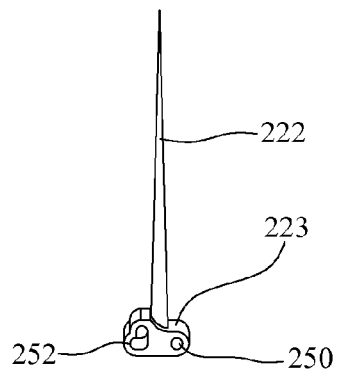
FIG. 15 is a side view of one of the grasping needles of the alternate plunger assembly of FIG. 11.
Figure 16:
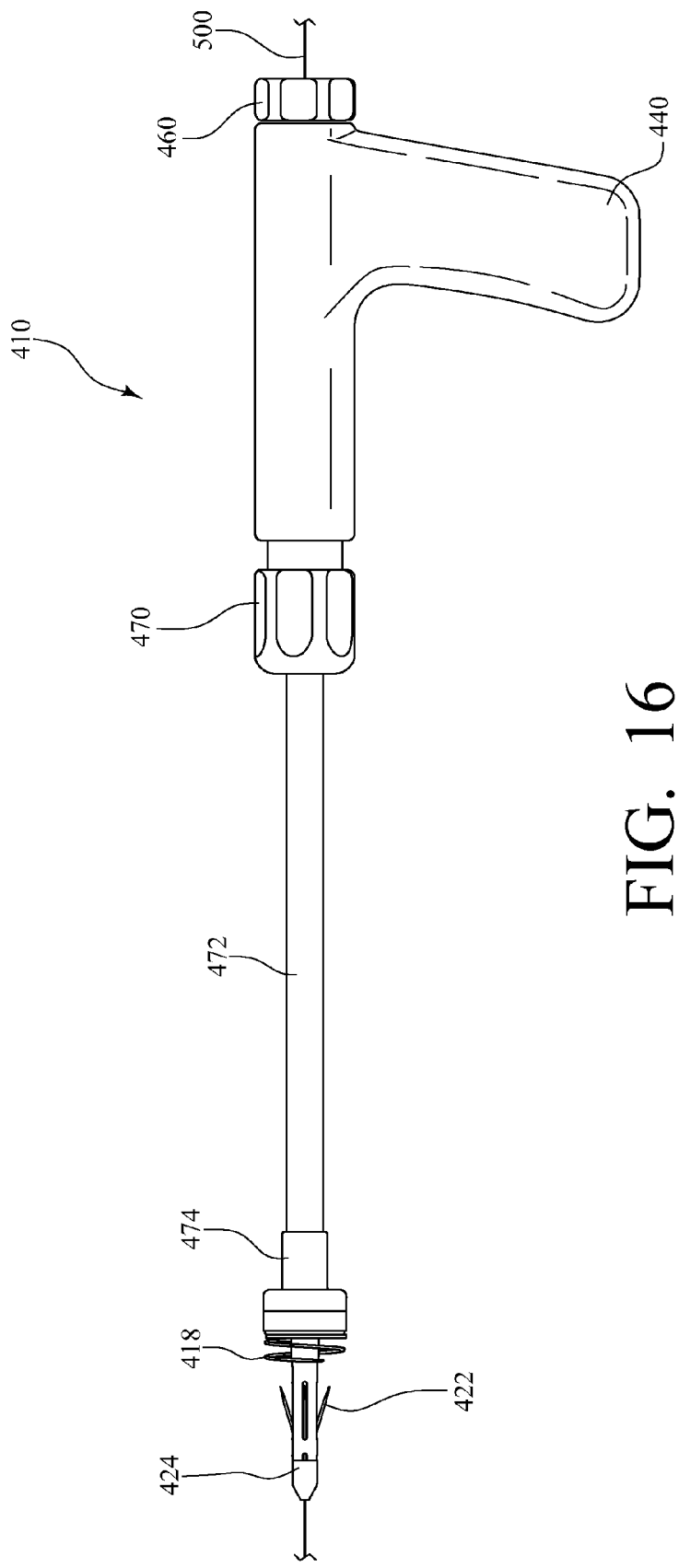
FIG. 16 is a side view of another exemplary endoscopic closure device made in accordance with the present invention.

FIGS. 13-15 are further views of the components of the plunger assembly 220. Referring first to FIG. 14, in this embodiment, the plunger 226 includes a base portion 240 and a plurality of projections 242 that extend upwardly from the base portion 240. These upwardly extending projections 242 define discrete cavities between one another, each such cavity for receiving a respective grasping needle 222. Furthermore, each of these upwardly extending projections 242 define a hole 244 therethrough.

Referring now to FIG. 15, each grasping needle 222 includes a hole 250 and a slot 252 defined through its base 223. The hole 250 of each grasping needle 222 is adapted to receive a ring 260. As illustrated in FIGS. 13 and 14, the ring 260 passes not only through the respective holes 250 of the grasping needles 222, but also passes through the corresponding holes 244 defined by the upwardly extending projections 242 of the plunger 226. Thus, the ring 260 effectively attaches the respective grasping needles 222 to the plunger 226, and the ring 260 further defines a pivot axis about which the base 223 of each grasping needle 222 can pivot as the grasping needles are moved from the storage position within the needle housing 224 (FIG. 12A) to the deployed position (FIG. 12B), or vice versa.

Figure 12A:
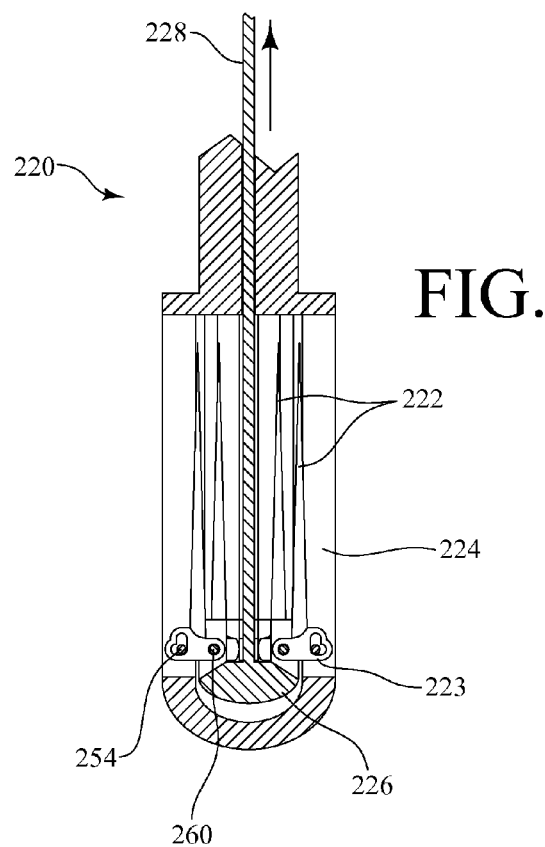
FIG. 12A is a sectional view of the alternate plunger assembly and needle housing of FIG. 11, with the grasping needles positioned within the needle housing in a storage position.
Figure 12B:
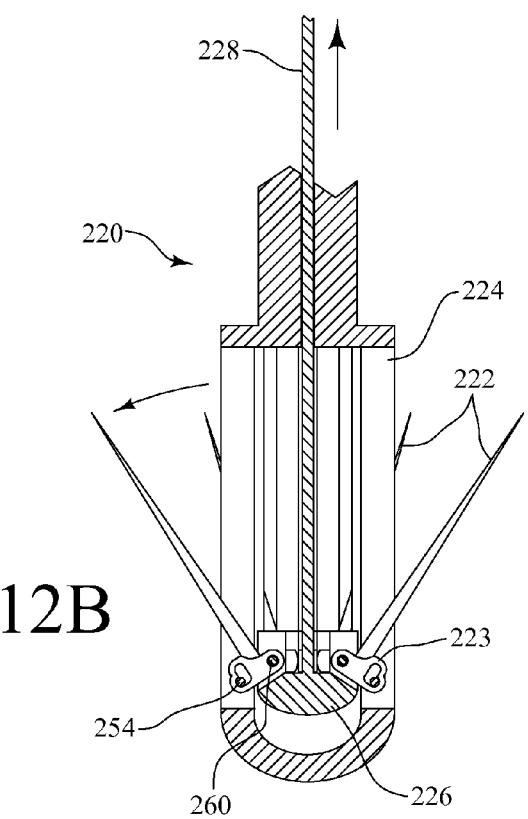
FIG. 12B is a sectional view of the alternate plunger assembly and needle housing similar to FIG. 12A, but with the grasping needles in a deployed position.

Referring now to FIG. 15 and the sectional views of FIGS. 12A and 12B, the slot 252 defined by each of the grasping needles 222 accommodates a pin connection 254 to the needle housing 224, which accommodates, but limits, the pivoting movement of each grasping needle 222 relative to the needle housing 224.

FIGS. 16-23 illustrate another exemplary endoscopic closure device 410 made in accordance with the present invention. In this embodiment, the various components of the endoscopic closure device 410 are arranged over a guide wire 500.

Figure 17:
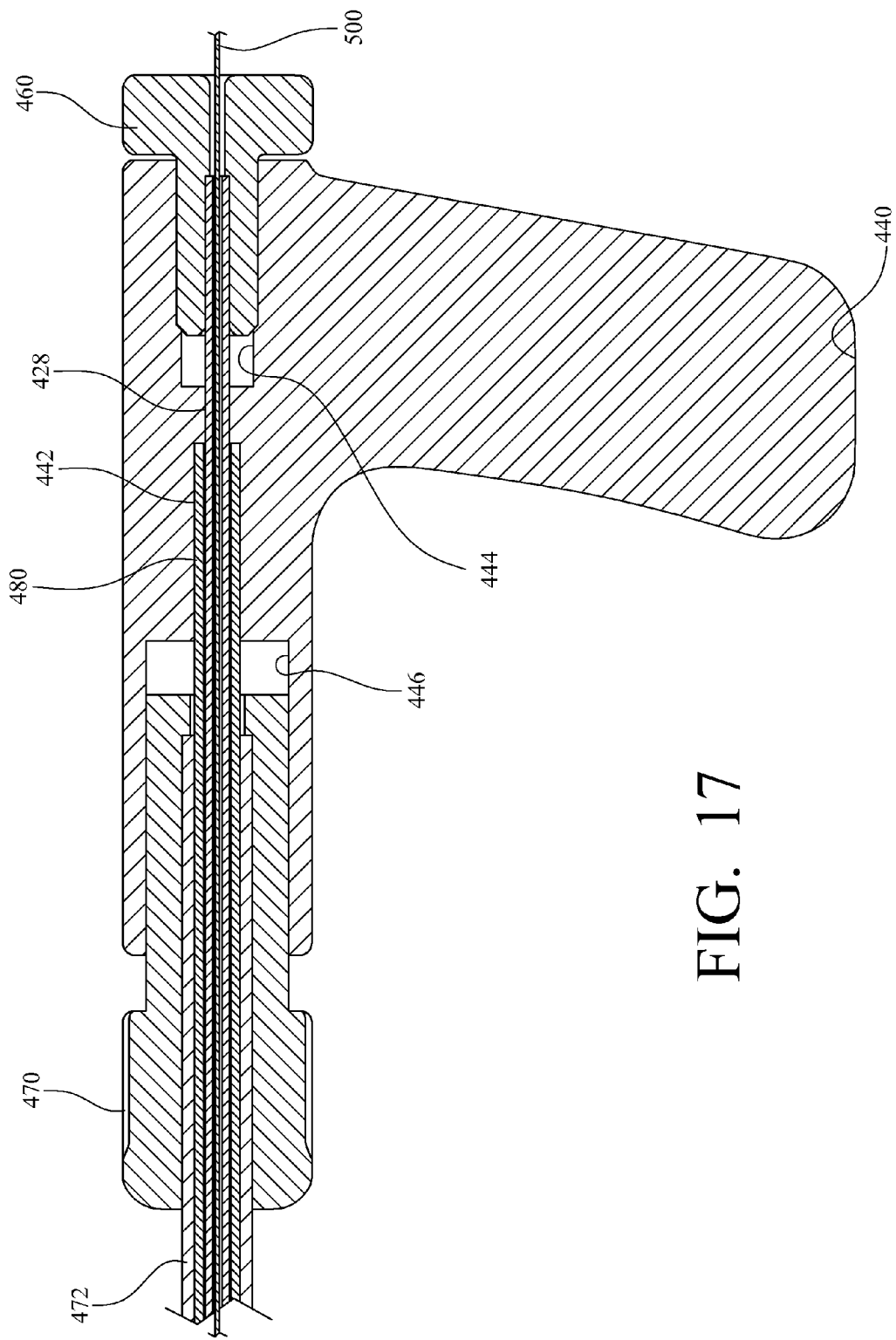
FIG. 17 is a partial sectional view of the exemplary endoscopic closure device of FIG. 16.

Referring now to the sectional view of FIG. 17, the exemplary endoscopic closure device 410 includes a handle portion 440. The handle portion 440 defines a central channel 442 along its length. Furthermore, at a first end of the central channel 442, the handle portion 440 defines a cavity 444 for receiving a first (or rear) adjustment knob 460, the function of which will be described below. At the opposite end of the central channel 442, the handle portion 440 defines a cavity 446 for receiving a second (or front) adjustment knob 470.

The second adjustment knob 470 is mounted for linear and rotational movement within the cavity 446 relative to the handle portion 440. Furthermore, the second adjustment knob 470 is connected to a first (or external) hollow shaft 472 that extends away from the handle portion 440 of the endoscopic closure device 410, such that the second adjustment knob 470 and the first hollow shaft 472 rotate together. Referring again to FIG. 16, a coupling member 474 is connected to the distal end of this first hollow shaft 472, and thus also moves and/or rotates with the second adjustment knob 470 and the first hollow shaft 472. Finally, a helical needle 418 is mounted to the coupling member 474.

Referring again to the sectional view of FIG. 17, the endoscopic closure device 410 also includes a second (or internal) hollow shaft 480 that is fixed to the handle portion 440 and then extends through the second adjustment knob 470 and through the first hollow shaft 472. Referring now to the sectional views of FIGS. 21-23, a needle housing 424 is connected to the distal end of the second hollow shaft 480.

Figure 18:
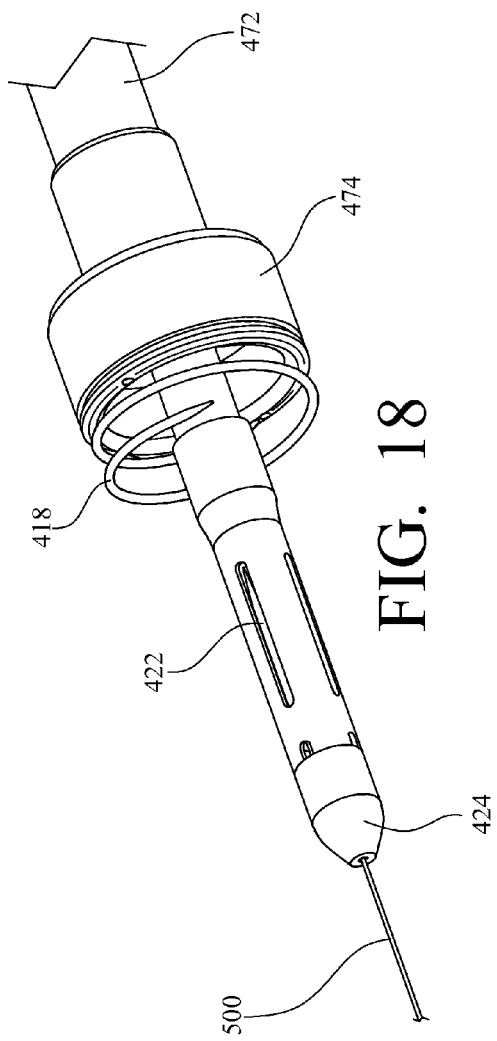
FIG. 18 is a partial perspective view of the exemplary endoscopic closure device of FIG. 16, with the grasping needles positioned within the needle housing in a storage position.
Figure 19:
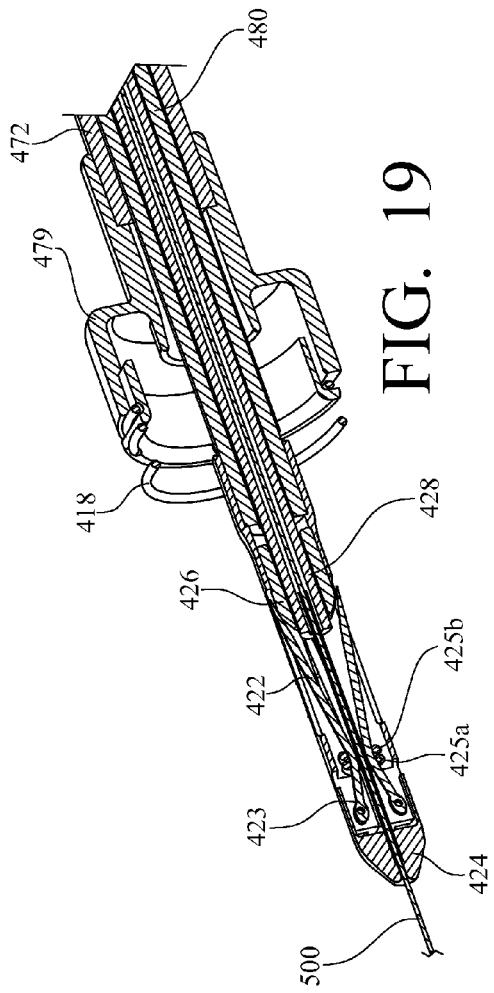
FIG. 19 is a sectional view of the exemplary endoscopic closure device of FIG. 16, with the grasping needles positioned within the needle housing in a storage position.

Returning again to the sectional view of FIG. 17, the first adjustment knob 460 is connected to a rod 428 that extends through the central channel 442 of handle portion 440, through the second hollow shaft 480, and into the needle housing 424, where it is connected to a plunger 426. As in the embodiments described above with respect to FIGS. 1-15, a plurality of grasping needles 422 is positioned within the needle housing 424 in a storage position, as illustrated in FIGS. 18 and 19. Furthermore, and as illustrated in FIG. 19, in this embodiment, the head of each grasping needle 422 is secured and held within a respective recess 423 defined by the needle housing 424. Then, one or more elastomeric rings 425a, 425b are positioned around the plurality of grasping needles 422 to bias them into the storage position.

Figure 20:
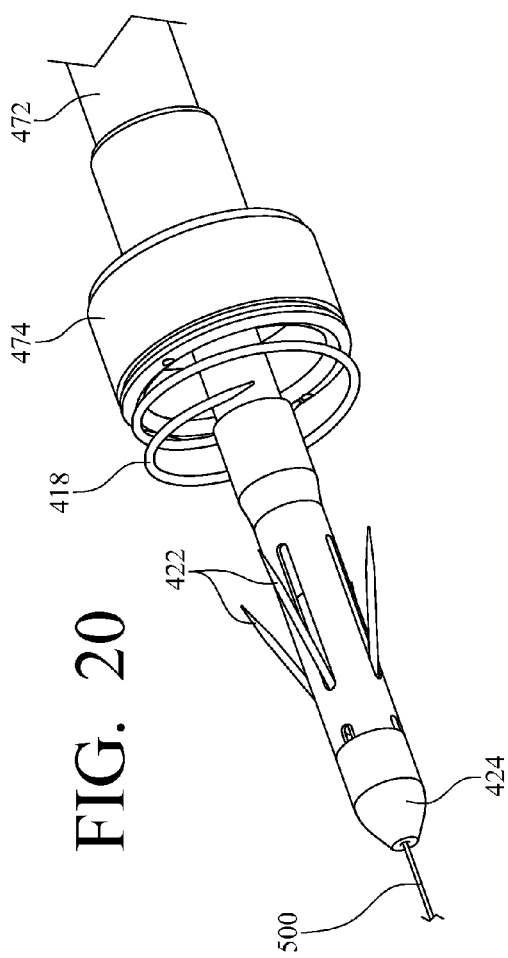
FIG. 20 is a partial perspective view of the exemplary endoscopic closure device of FIG. 16, with the grasping needles in a deployed position.
Figure 21:
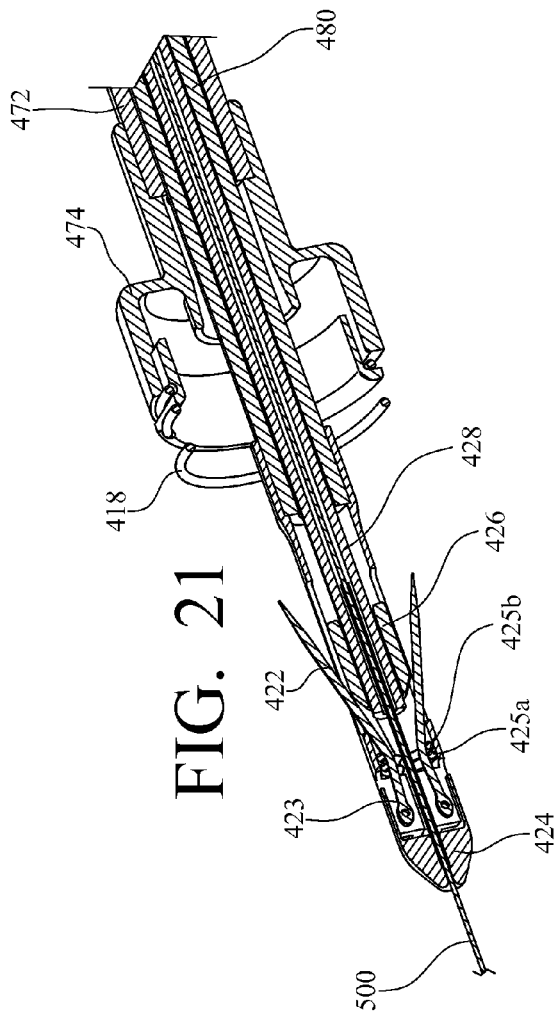
FIG. 21 is a sectional view of the exemplary endoscopic closure device of FIG. 16, with the grasping needles in a deployed position.

The plunger 426 is adapted for movement within and along the longitudinal axis of the needle housing 424. By moving the plunger 426 downward, it engages and moves the grasping needles 422, which are preferably constructed of a substantially flexible metal (such as nitinol, an alloy of nickel and titanium), from the storage position within the needle housing 424 (FIGS. 18-19) to the deployed position in which they extend through the walls of the needle housing 424 (FIGS. 20-21). Of course, once the plunger 426 is moved upward (or retracted), the grasping needles 422 will return to the storage position as a result of the biasing force of the elastomeric rings 425a, 425b.

Returning again to the sectional view of FIG. 17, with respect to the movement of the plunger 426, such movement is controlled by the first adjustment knob 460. As described above, the first adjustment knob 460 is received in a cavity 444 defined by the handle portion 440. By advancing the first adjustment knob 460 into the cavity 444 relative to the handle portion 440, the plunger 426 is moved downward to engage and move the grasping needles 422. In FIG. 17, which is a partial sectional view of FIG. 16, the grasping needles 422 have been moved to the deployed position, so the external portion of the adjustment knob 460 abuts the rear portion of the handle portion 440.

Alternatively, the first adjustment knob 460 may be provided with threads (not shown) that mate with corresponding threads (not shown) defined by the handle portion 440. Thus, by turning the first adjustment knob 460 in one direction (e.g., clockwise), the first adjustment knob 460 advances into the handle portion 440 and moves the plunger 426 downward to engage and move the grasping needles 422. By turning the first adjustment knob 460 in the opposite direction (e.g., counterclockwise), the plunger 426 is moved upward and away from the grasping needles 422, and the grasping needles return to the storage position.

As with the embodiments described above with respect to FIGS. 1-15, in practice, the endoscopic closure device 410 is placed in proximity to the luminal defect. Unlike the above-described embodiment, however, the positioning of this endoscopic closure device 410 may be facilitated thorough the use of a guide wire 500. Specifically, once the guide wire 500 is properly positioned, the endoscopic closure device 410 can be advanced over the guide wire 500.

As the endoscopic closure device 410 is advanced into position, the needle housing 424 is extended into the luminal defect, with a user grasping and manipulating the handle portion 440 of the endoscopic closure device 410 to position it in the luminal defect, with the needle housing 424 below the surface of the surrounding tissue. The plunger 426 is then moved downward by advancing (or turning) the first adjustment knob 460, as described above. The plunger 426 thus engages and moves the grasping needles 422 to the deployed position in which the grasping needles 422 extend through the walls of the needle housing 424, as illustrated in FIGS. 20-21. The user can then pull up on the handle portion 440 of the endoscopic closure device 410 to pull and draw the tissue surrounding the luminal defect together with the grasping needles 422.

Figure 22:
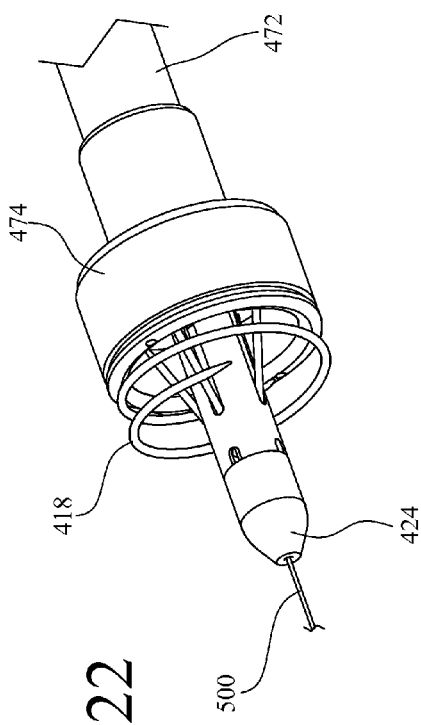
FIG. 22 is a partial perspective view of the exemplary endoscopic closure device of FIG. 16, with the grasping needles in a deployed position and the helical needle advanced toward the grasping needles.
Figure 23:
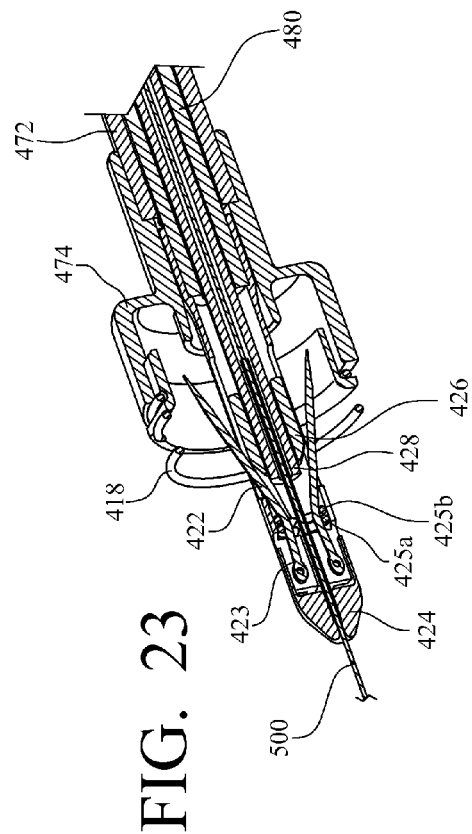
FIG. 23 is a sectional view of the exemplary endoscopic closure device of FIG. 16, with the grasping needles in a deployed position and the helical needle advanced toward the grasping needles.

Next, the user can manipulate the second adjustment knob 470, moving it downward and away from the handle portion 440 of the endoscopic closure device 410. Since the second adjustment knob 470 is connected to the first hollow shaft 472, which, in turn, is connected to the coupling member 474, the helical needle 418 is thus advanced toward the grasping needles 422, as illustrated in FIGS. 22-23. And, as a result, the surrounding tissue is now within a cylindrical cavity bounded by the helical needle 418.

Then, by rotating the second adjustment knob 470 relative to the handle portion 440, the first hollow shaft 472 and the coupling member 474 are also rotated, so that the helical needle 418 is driven into and pierces the tissue, carrying a suture through the tissue. Again, as with the embodiments described above with respect to FIGS. 1-15, the helical needle 418 passes through the tissue multiple times, thus creating a "purse string" suture.

One of ordinary skill in the art will recognize that additional embodiments are possible without departing from the teachings of the present invention or the scope of the claims which follow. This detailed description, and particularly the specific details of the exemplary embodiments disclosed herein, is given primarily for clarity of understanding, and no unnecessary limitations are to be understood therefrom, for modifications will become obvious to those skilled in the art upon reading this disclosure and may be made without departing from the spirit or scope of the claimed invention.

What is claimed is:

1. An endoscopic closure device, comprising:
   a coupling member;
   a helical needle mounted to the coupling member and carrying a suture; and
   a plurality of grasping needles, each of said plurality of grasping needles moveable between a storage position and a deployed position;
   a plunger assembly adapted for movement relative to the coupling member along a longitudinal axis of the endoscopic closure device, said plunger assembly including (a) a needle housing, wherein the grasping needles are positioned within the needle housing in the storage position, (b) a plunger adapted for movement along a longitudinal axis of the plunger assembly, and (c) a rod connected to the plunger for effectuating movement of the plunger along the longitudinal axis of the plunger assembly;
   wherein said plurality of grasping needles is configured to be (a) advanced in the storage position within the needle housing into a luminal defect, (b) moved into the deployed position by a pushing action on the rod, such that the plunger engages and moves the grasping needles to the deployed position in which the grasping needles extend through one or more walls of the needle housing and surround the luminal defect, and (c) then retracted from the luminal defect, thus pulling and drawing tissue surrounding the luminal defect together within a cylindrical cavity bounded by the helical needle; and
   wherein, upon rotation of the coupling member and the helical needle, the helical needle is driven into and pierces the tissue, carrying the suture through the tissue around the luminal defect and effectively closing the luminal defect.

2. The endoscopic closure device as recited in claim 1, and further comprising an outer sheath, said coupling member adapted for rotational movement within and relative to the outer sheath.

3. The endoscopic closure device as recited in claim 1, wherein each of said plurality of grasping needles is composed of a substantially flexible metal.

4. The endoscopic closure device as recited in claim 1, wherein the suture includes a T-tag at its distal end, and wherein the helical needle is hollow with an opening at its distal end adapted to receive the T-tag of the suture.

5. The endoscopic closure device as recited in claim 1, wherein the suture includes a conical T-tag at its distal end, wherein the conical T-tag of the suture is positioned at a distal end of the helical needle as the helical needle is rotated and driven into the tissue.

* * * * *